(12) United States Patent
Fischer et al.

(10) Patent No.: US 6,765,118 B2
(45) Date of Patent: Jul. 20, 2004

(54) METHOD FOR THE PRODUCTION OF ALCOHOLS ON RHENIUM-CONTAINING ACTIVATED CHARCOAL SUPPORTED CATALYSTS

(75) Inventors: Rolf-Hartmuth Fischer, Heidelberg (DE); Rolf Pinkos, Bad Dürkheim (DE); Stephan Andreas Schunk, Heidelberg (DE); Joachim Wulff-Döring, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/239,409

(22) PCT Filed: Mar. 23, 2001

(86) PCT No.: PCT/EP01/03374
§ 371 (c)(1),
(2), (4) Date: Sep. 23, 2002

(87) PCT Pub. No.: WO01/70657
PCT Pub. Date: Sep. 27, 2001

(65) Prior Publication Data
US 2003/0050516 A1 Mar. 13, 2003

(30) Foreign Application Priority Data
Mar. 24, 2000 (DE) ........................................ 100 14 646

(51) Int. Cl.⁷ ............................................... C07L 27/00
(52) U.S. Cl. ........................ 568/864; 568/799; 568/811
(58) Field of Search ................................. 568/864, 799, 568/811

(56) References Cited

U.S. PATENT DOCUMENTS 4,609,636 A * 9/1986 Mabry et al.
4,804,791 A * 2/1989 Kitson
4,973,717 A * 11/1990 Williams
4,985,572 A * 1/1991 Kitson
5,149,680 A * 9/1992 Kitson
5,698,749 A    12/1997 Pedersen et al. ............. 568/864
6,008,384 A    12/1999 Bockrath et al. ........... 549/508
6,294,703 B1 * 9/2001 Hara
6,486,367 B1 * 11/2002 Budge

FOREIGN PATENT DOCUMENTS

| EP | 0 319 116 | 6/1989 |
| EP | 0 373 938 | 6/1990 |
| EP | 0 589 168 | 3/1994 |
| EP | 0 848 991 | 6/1998 |
| GB | 1 551 741 | 8/1979 |
| JP | 2001-2605 | * 1/2001 |

OTHER PUBLICATIONS

Broadbent et al. "Rhenium and its compounds as hydrogenation catalysts" J. Org. Chem. vol. 24 (1959) pp. 1847–1854.

Timogeev et al. "Hydrogenation of maleic anhydride in the presence of platinum group metals and rhenium" Chem Abstr. 95; 80602 (1981).

* cited by examiner

*Primary Examiner*—Michael L. Shippen
(74) *Attorney, Agent, or Firm*—Keil & Weinkauf

(57) ABSTRACT

In a process for the preparation of alcohols by catalytic hydrogenation of carbonyl compounds, the catalyst used is 0.01 to 50% by weight of rhenium and 0 to 20% by weight, in each case based on the total weight of the catalyst, of at least one further metal chosen from Zn, Cu, Ag, Au, Ni, Fe, Cr, V on oxidatively pretreated activated carbon as support.

10 Claims, No Drawings

METHOD FOR THE PRODUCTION OF ALCOHOLS ON RHENIUM-CONTAINING ACTIVATED CHARCOAL SUPPORTED CATALYSTS

The invention relates to a process for the preparation of alcohols by hydrogenation of compounds containing carbonyl groups over Re-containing oxidatively pretreated activated carbon supported catalysts with the avoidance of the formation of ethers.

The industrial preparation of alcohols frequently uses starting materials containing carbonyl groups, such as aldehydes, ketones, carboxylic acids, carboxylic anhydrides and esters, which are hydrogenated with hydrogen.

More recently, particularly active catalysts in this connection have been found using oxidatively pretreated activated carbon supports. EP-A-0 848 991 describes a catalyst containing palladium, silver, rhenium and iron, which can, for example, hydrogenate maleic acid or esters thereof to give butanediol. During the hydrogenation of maleic acid at 100 to 162° C., a selectivity to butanediol of 89.5% is achieved. The hydrogenation success is diminished by the fact that 5.6% of tetrahydrofuran (THF) forms as byproduct as ether. In addition, n-butanol is also formed as a further byproduct in an amount of 4%.

U.S. Pat. No. 5,698,749 describes catalysts which contain an element of group VIII and at least rhenium, tungsten or molybdenum on an oxidatively pretreated carbon support. In particular, Pd/Re/C and Pd/Re/Ag/C catalysts are described. Using these catalysts, in the hydrogenation of aqueous maleic acid THF again forms in addition to butanediol. Here, butanediol is obtained with a selectivity up to 92.8%. However, THF still forms in an amount of 1.6%, and the further byproduct n-butanol in an amount of 4.6%.

The tendency of the hydrogenation metals rhenium and platinum to form THF and thus ether during the hydrogenation of maleic acid derivatives is known (see e.g. A. F. Timofeev et al., Prikl. Khim. (Leningrad) 1981, 54 (2), 335–8, Chemical Abstracts 95: 80602 X). The same effect is also described in GB-A-1 551 741 using supported Pd/Re, Pt/Re or Pt/Pd/Re catalysts.

In J. Org. Chem. 24, 1847–1854 (1959), H. S. Broadbent et al. describe the hydrogenation of succinic acid over unsupported metallic Re, in which considerable amounts of THF are formed.

However, the avoidance of ethers as byproduct in industrial hydrogenation processes is desirable since their formation reduces the efficiency of the process. In addition, the ethers can sometimes only be removed from the desired product with difficulty. Moreover, the ethers entail considerable disposal costs since they, such as e.g. THF, must no longer be introduced into a water treatment plant, even in small amounts, because they are not readily biodegradable.

It is an object of the present invention to provide rhenium catalysts with which carbonyl compounds can be hydrogenated to give alcohols with high overall selectivity, preferably without the formation of ethers.

We have found that this object is achieved by the fact that carbonyl compounds can be catalytically hydrogenated to give the corresponding alcohols without ether formation if a catalyst comprising 0.01 to 50% by weight of rhenium and 0 to 20% by weight, in each case based on the total weight of the catalyst, of at least one further metal chosen from Zn, Cu, Ag, Au, Ni, Fe, Cr, V on oxidatively pretreated activated carbon as support is used for the hydrogenation.

In this connection, without ether formation means that the ether formation should amount to no more than 0.5% of the hydrogenation products. The ether proportion is preferably below 0.2%, particularly preferably below 0.1%.

The invention relates to a process for the preparation of alcohols by catalytic hydrogenation of carbonyl compounds in which the catalyst used is 0.01 to 50% by weight of rhenium and 0 to 20% by weight, in each case based on the total weight of the catalyst, of at least one further metal chosen from Zn, Cu, Ag, Au, Ni, Fe, Cr, V on oxidatively pretreated activated carbon as support, and to the corresponding catalyst and its use in the catalytic hydrogenation of carbonyl compounds.

The additional elements can modify the catalyst essentially in terms of the activity and selectivity with regard to the hydrogenolysis products. However, they are not essential.

The proportion of rhenium (calculated as metal) is preferably 0.1 to 20% by weight, particularly preferably 1 to 15% by weight, based on the total weight of the catalyst.

In particular, a catalyst is used which consists only of rhenium on oxidatively pretreated activated carbon as support.

The catalyst is preferably arranged as a fixed bed.

In general, suitable activated carbons are the commercially available activated carbons. Preference is given to using those which contain little chlorine and sulfur and whose micropore proportion is as low as possible. The oxidative treatment of the activated carbons can be carried out using customary oxidizing agents. Examples which may be mentioned are nitric acid, hydrogen peroxide, sodium perborate, oxygen, air, ozone, ammonium persulfate, sodium hypochloride or hypochlorous acid, perchloric acid and salts of nitric acid, such as sodium nitrate or platinum nitrate. Preference is given to nitrates, sodium perborate, hydrogen peroxide and air.

The treatment of the activated carbon with the oxidizing agent can be carried out before or else during the application of the rhenium component or further catalyst components. Suitable processes are also described in U.S. Pat. No. 5,698,749 and EP-A-0 848 991.

The rhenium component used is usually $Re_2O_7$, $ReO_2$, $ReCl_3$, $ReCl_5$, $Re(CO)_5Cl$, $Re(CO)_5Br$ or $Re(CO)_{10}$. Preference is given to using $Re_2O_7$.

In a preferred embodiment, platinum is also applied to the catalyst in addition to rhenium. The platinum can be applied, for example, as platinum powder, oxide, oxide hydrate, nitrate, platinum(II) or (IV) chloride, hexachloroplatinic acid, platinum(II) or (IV) bromide, platinum(II) iodide, cis- or trans-diamminedichloroplatinum(II), cis- or trans-diamminetetrachloroplatinum(IV), diamminedinitroplatinum(II), dichloro(ethylenediamine) platinum(II), tetraammineplatinum(II) chloride or tetraammineplatinum(II) chloride hydrate, tetraammineplatinum(II) nitrate, tetrakis (triphenylphosphine)platinum(0), cis- or trans-dichlorobis (triethylphosphine)platinum(II), cis- or trans-platinum(II) bis(triethylphosphine) oxalate, platinum(IV) bis (triethylphosphine) oxide, dichloro(2,2'-6',2"-terpyridine) platinum(II) dihydrate, cis-bis(acetonitrile)platinum dichloride, cis-bis(benzonitrile)platinum dichloride, platinum(II) acetylacetonate, platinum(II) 1c.5c-cyclooctadiene chloride or bromide, preferably as platinum oxide or nitrate, particularly preferably as platinum nitrate.

The active components, in particular Re, can be applied by impregnation in one or more steps with an aqueous or alcoholic solution of the dissolved salts in each case, impregnation with a solution of dissolved oxidic or metallic colloid of the active components, equilibrium adsorption in one or more steps of the salts dissolved in aqueous or alcoholic solution, or equilibrium adsorption of dissolved oxidic or metallic colloid on the pretreated activated carbon. In this process, the active components can be applied to the activated carbon either simultaneously or successively. In each case, a drying step is carried out between the individual impregnation and equilibrium adsorption steps to remove the solvent. The active components are preferably applied by impregnation with an aqueous salt solution or an aqueous oxidic colloid in one step.

To remove the solvent after the impregnation and equilibrium adsorption step, the impregnated catalyst is dried. The drying temperature here is 30–350° C., preferably 40–280° C., particularly preferably 50–150° C.

The catalysts are usually activated prior to use. Hydrogen is preferably used for this purpose. The activation temperature here is 100–500° C., preferably 130–400° C., particularly preferably 150–350° C.

The hydrogenation is carried out at 50–250° C., preferably 60–220° C., particularly preferably 70–190° C., very particularly preferably 80–140° C. The hydrogenation is carried out here at a reaction pressure between 3 and 330 bar, preferably 20 and 300 bar, particularly preferably 30 and 300 bar. Here, the pressure range during the hydrogenation is preferably greater than 150 bar in the liquid phase in the fixed bed, 3 to 100 bar in the fixed bed in the gas phase and 10 to 90 bar in the suspension.

Suitable starting materials for the hydrogenation are generally carbonyl compounds, such as aldehydes, carboxylic acids or esters or anhydrides thereof, or lactones which may additionally contain C—C double or triple bonds. Examples of aldehydes are propionaldehyde, butyraldehyde, crotonaldehyde, ethylhexanal, nonanal and glucose. Examples of carboxylic acids are succinic acid, fumaric acid, maleic acid, glutaric acid, adipic acid, 6-hydroxycarboxylic acid, octanedioic acid, dodecanedioic acid, 2-cyclododecylpropionic acid and saturated or unsaturated fatty acids. Esters which may be mentioned are esters of the abovementioned acids, e.g. methyl, ethyl, propyl or butyl esters, and lactones can also be used, e.g. gamma-butyrolactone, delta-valerolactone or caprolactone. It is also possible to use anhydrides, such as succinic anhydride or maleic anhydride. Preferred starting materials are succinic acid, maleic acid, adipic acid, 2-cyclododecylpropionic acid, succinic anhydride, maleic anhydride, and the esters of these acids and gamma-butyrolactone. The products which can be obtained are, inter alia, 1-4-butanediol, 1,6-hexanediol and 2-cyclododecylpropan-1-ol.

The compounds to be hydrogenated can be hydrogenated without a diluent or in solution. A possible solvent is, for example, the hydrogenation product itself, or substances which are inert under the reaction conditions are used, such as alcohols, e.g. methanol, ethanol, propanol or butanol. Ethers, such as THF or ethylene glycol ether, are also suitable. A preferred solvent is water, in particular in the hydrogenation of carboxylic acids. The hydrogenation can be carried out in the gas or liquid phase and in one or more stages. In the liquid phase, both the suspension and the fixed-bed procedures are possible. In the case of exothermic reactions, the heat can be dissipated by external cooling means (e.g. tubular reactor). In addition, evaporative cooling in the reactor is possible, especially if the hydrogenation is carried out without product recycle. If the product is recycled, a condenser in the recycle stream is suitable.

The hydrogenation is preferably carried out in the liquid phase at a pressure in the range from 150 to 300 bar and a temperature in the range from 80 to 140° C. Here, the catalyst is used, in particular, in the form of a fixed bed.

The alcohols obtained in the process according to the invention are used, for example, as solvents and intermediates. Diols, such as butanediol, are used as diol component in polyesters. 2-cyclododecylpropan-1-ol is a sought-after musk fragrance.

The process according to the invention is described in more detail by reference to the examples below. The stated contents of the individual components in the hydrogenation products have been determined by gas chromatography. Unless stated otherwise, they are calculated on a solvent-free basis.

EXAMPLES

Example 1

20 g of activated carbon (1–3 mm chips) were oxidized with 65% $HNO_3$ and dried at 120° C. 18 g of the carbon pretreated in this way were impregnated with 5 g of $Re_2O_7$ as aqueous solution and dried at 120° C. The catalyst obtained in this way was then activated with a stream of hydrogen for 40 h at 270° C. and ambient pressure. 25 ml of the activated catalyst were then charged to a 25 ml-capacity reactor. The hydrogenation was carried out in trickle mode without product recycle, the feed being about 20 g/h. The reaction pressure was 220 bar, and approximately 100 l (STP) of hydrogen/h were introduced. A 5% strength maleic acid solution in water was started at a temperature of 174° C. After an experiment time of. 27 h, the discharge comprised about 96.5% of butanediol and 3.5% of n-butanol. After the temperature had been reduced to 166° C., after a total experiment time of 45 hours the hydrogenation discharge comprised about 97.1% of butanediol, 0.9% of gamma-butyrolactone and 2% of n-butanol. After the maleic acid concentration in the feed had been increased to 20%, at 166° C. and a total running time of 55 h, 95.7% of butanediol, 2.5% of gamma-butyrolactone and 1.5% of n-butanol were found. No THF was detected in the hydrogenation discharge throughout the entire experiment time.

Example 2

Analogously to Example 1, 20 g of activated carbon (Epibon® Spezial, from Lurgi) were pretreated with $HNO_3$ and impregnated with 5 g of $Re_2O_7$ and 15 g of platinum nitrate solution (=2.5% $PtO_2$) and dried. The procedure was then continued as in Example 1 except that after an experiment time of 24 h, a switch was made to a 30% strength maleic acid solution. After a total experiment time of 78 h, at a reaction temperature of about 100° C., about 97.3% of butanediol and 2.5% of n-butanol, but no THF, were found in the discharge.

We claim:

1. A process for the preparation of alcohols by catalytic hydrogenation of carbonyl compounds, which comprises using a catalyst consisting of, 0.01 to 50% by weight of rhenium and 0 to 20% by weight, in each case based on the total weight of the catalyst, of at least one further metal chosen from Zn, Cu, Ag, Au, Ni, Fe, Cr, V on oxidatively pretreated activated carbon as support, whereby the process is carried out without ether formation.

2. A process as claimed in claim 1, wherein the catalyst used consists of 0.1 to 20% by weight of rhenium, based on the total weight of the catalyst, on oxidatively pretreated activated carbon as support.

3. A process as claimed in claim 1, wherein the catalyst is arranged as a fixed bed.

4. A process as claimed in claim 1, wherein the carbonyl compound is chosen from aldehydes, carboxylic acids or esters or anhydrides thereof, or lactones.

5. A process as claimed in claim 4, wherein the carbonyl compound is chosen from maleic acid, fumaric acid, succinic acid or esters or anhydrides thereof, or gamma-butyrolactone, and is hydrogenated to give 1,4-butanediol.

6. A process as claimed in claim 1, wherein the hydrogenation is carried out in the liquid phase at a pressure in the range from 150 to 300 bar and at a temperature in the range from 50 to 250° C.

7. A process as claimed in claim 1, wherein the oxidatively pretreated activated carbon which is used as support in the process isl prepared by an oxidative treatment of an activated carbon with an oxidizing agent which is selected from the group consisting of nitrates, sodium perborate, hydrogen peroxide and air.

8. A process as claimed in claim 1, wherein the catalyst is prepared by impregnating the oxidatively pretreated activated carbon with an aqueous or alcoholic solution of the dissolved rhenium component.

9. A process as claimed in claim 1, wherein the catalyst is activated prior to use by hydrogen and a temperature of 100–500° C.

10. A process for the preparation of alcohols by catalytic hydrogenation of carbonyl compounds, which comprises using a catalyst consisting of 0.01 to 50% by weight of rhenium and 0 to 20% by weight, in each case based on the total weight of the catalyst, of at least one further metal chosen from Zn, Cu, Ag, Au, Cr, V or oxidatively pretreated activated carbon as support.

* * * * *